United States Patent
Mathis et al.

(10) Patent No.: US 6,878,552 B1
(45) Date of Patent: Apr. 12, 2005

(54) HOMOGENEOUS DETECTION AND/OR DETERMINATION METHOD FOR A CHEMICAL OR PHYSICO-CHEMICAL INTERACTION

(75) Inventors: Gérard Mathis, Bagnols sur Ceze (FR); Hervé Bazin, Villeneuve les Avignon (FR)

(73) Assignee: Cis Bio International French Joint Stock Company, Saclay (FR)

( * ) Notice: Subject to any disclaimer, the term of this patent is extended or adjusted under 35 U.S.C. 154(b) by 0 days.

(21) Appl. No.: 09/958,136

(22) PCT Filed: Apr. 7, 2000

(86) PCT No.: PCT/FR00/00887

§ 371 (c)(1),
(2), (4) Date: Oct. 5, 2001

(87) PCT Pub. No.: WO00/62072

PCT Pub. Date: Oct. 19, 2000

(30) Foreign Application Priority Data

Apr. 8, 1999 (FR) ............................................. 99 04382

(51) Int. Cl.⁷ .......................... G01N 21/64; G01N 33/58
(52) U.S. Cl. ............................ 436/172; 436/94; 436/86; 436/87; 436/93; 436/95; 436/166; 435/6; 435/7.1
(58) Field of Search ........................... 436/172, 94, 86, 436/87, 93, 95, 166; 435/6, 7.1

(56) References Cited

U.S. PATENT DOCUMENTS

| | | | | |
|---|---|---|---|---|
| 5,262,299 A | * | 11/1993 | Evangelista et al. ........... | 435/6 |
| 5,432,101 A | * | 7/1995 | Mathis et al. ................ | 436/546 |
| 5,457,185 A | * | 10/1995 | Lehn et al. ................... | 534/15 |
| 5,827,653 A | * | 10/1998 | Sammes et al. ............... | 435/6 |
| 6,340,747 B1 | * | 1/2002 | Bazin et al. ................ | 536/23.1 |
| 6,344,360 B1 | * | 2/2002 | Colvin et al. ................ | 436/94 |

FOREIGN PATENT DOCUMENTS

| | | | |
|---|---|---|---|
| WO | WO98/15830 | * | 4/1998 |
| WO | WO99/18114 | * | 4/1999 |

* cited by examiner

*Primary Examiner*—Jeffrey R. Snay
(74) *Attorney, Agent, or Firm*—Millen, White, Zelano, Branigan, P.C.

(57) ABSTRACT

The invention relates to a homogeneous method for detecting and/or determining by fluorescence a chemical or physicochemical interaction in a measuring medium, in which a rare-earth metal cryptate comprising a substituent is used, characterized in that the variation of at least one fluorescence characteristic of the rare-earth metal cryptate, induced by the change in the physicochemical properties of the substituent resulting from said interaction, is measured.

16 Claims, 1 Drawing Sheet

FIG.1

FIG.2

HOMOGENEOUS DETECTION AND/OR DETERMINATION METHOD FOR A CHEMICAL OR PHYSICO-CHEMICAL INTERACTION

The invention relates to a homogeneous method for detecting and/or determining by fluorescence a chemical or physicochemical interaction in a measuring medium, in which a rare-earth metal cryptate comprising a substituent is used, characterized in that the variation of at least one fluorescence characteristic of the rare-earth metal cryptate, induced by the change in the physicochemical properties of the substituent resulting from said interaction, is measured.

In biology, it is advantageous to be able to measure or study the activity of various enzymes or an interaction between biomolecules, which are key events in understanding cell phenomena and in the search for new molecules or active principles.

"Homogeneous methods" (for measuring activity of or binding without isolating the biomolecules studied from the medium) are particularly advantageous since they allow the study or measuring process to be automated.

Methods using fluorescence are particularly sensitive, but are liable to be disturbed by the optical properties of the medium.

A homogeneous method using rare-earth metal cryptates is particularly advantageous, but requires the use of two labels (G. Mathis et al., Clin. Chem., 1993, 39, 1251).

In patent application WO 91/108490, the various activities of the enzymes to be studied are cleverly used to provide a chemical modification to a substrate molecule which is capable, or becomes capable, of forming a complex in solution with a rare earth metal.

This method makes it possible in principle to detect several types of enzymatic activity in a homogeneous phase. In practice, the formation in situ of the complex with the rare-earth metal (in the presence of the biological medium) is a major handicap since the medium may contain molecules which compete with the modified substrate to form the complex.

This technique is used above all in heterogeneous assays in which the activity of an enzyme used as tracer (ELISA) is measured, during the study of the photophysical properties of various cryptates and in particular of cryptates bearing on substituents attached to donor molecular units.

It has now been found that a chemical or physicochemical interaction capable of modifying a substituent bound to a rare-earth metal cryptate can cause changes in the coordination environment of the rare-earth metal ion and consequently modify the phytophysical properties of the cryptate.

The object of the invention is thus to use these changes in the coordination environment of a rare-earth metal ion in a cryptate to detect or measure an enzymatic activity or a biological interaction in a homogeneous phase.

Advantageously, such a method requires only one fluorescent marker, namely the rare-earth metal cryptate.

In particular, said change has an influence on the salvation sphere of the rare-earth metal ion.

Said fluorescence characteristic is chosen, for example, from the emission lifetime, the fluorescence intensity, the distribution of the lines in the fluorescence spectrum and the polarization.

The variation measured in the method according to the invention may be, for example, an increase or decrease in the emission lifetime or in the fluorescence intensity, and may be due in particular to an agent inducing a fluorescence enhancement or extinction.

According to one advantageous aspect of the method according to the invention, said substituent is negatively charged or acquires a negative charge during a physico-chemical process.

In the present description, the term "substituent" means either a chemical group such as, for example, a phosphate, phosphonate or carboxylate group or a derivative thereof, for example an ester or amide group, or a chemical or biological molecule comprising such a group, such as, for example, a nucleic acid, an oligonucleotide or an oligonucleotide consisting of or comprising nucleotide analogs; a nucleotide or a nucleoside and analogs thereof.

The interaction which it is desired to detect may result, for example, from an enzymatic reaction, in particular involving enzymes such as phosphatase, phosphodiesterase, esterase, exonuclease, deoxyribunuclease, ribonuclease, ligase, kinase or polymerase.

Said interaction may also, according to another aspect of the invention, consist of a hybridization or denaturing reaction of nucleic acids, of oligonucleotides or of oligonucleotides consisting of or comprising nucleotide analogs, or of a reaction between said nucleic acids or oligonucleotides with proteins having an affinity for them.

The term nucleotide or oligonucleotide "analog" means molecules differing from the corresponding natural molecules by a change in their structure, such as optical isomers (for example α configuration of the base relative to the sugar), positional isomers (for example 2'–5' sequences of phosphate bridges), or by a change in the substituents of the base (for example diaminopurine) or of the sugar (for example 3'-deoxyribose).

These oligonucleotides may consist, for example, of a sequence of ribonucleotide or deoxyribonucleotide units or of nucleotide analog units modified on the sugar or on the base and linked together by natural internucleotide linkages of phosphodiester type, some of the internucleotide linkages possibly being replaced with phosphonate, phosphoramide or phosphorothioate linkages. These various families of oligonucleotides are described in Goodchild, *Bioconjugate Chemistry*, 1(3), May/June 1990, 77–99.

These oligonucleotides may also consist of a sequence comprising both ribonucleotide or deoxyribonucleotide units linked together via linkages of phosphodiester type and nucleoside analog units linked together via amide linkages, which are commonly known as "PNA" (peptide nucleic acid", as described in M. Egholm et al., J. Am. Chem. Soc., 1992, 114, 1895–1897; such compounds are described, for example, in R. Vinayak et al., nucleoside & Nucleotide, 1997, 16 (7–9), 1653–1656.

The method according to the invention makes it possible in particular to study, in real time, the kinetic aspects of an interaction between molecules, for example hybridization, the fact of using only one fluorescent marker considerably simplifying the implementation of said method.

In one advantageous aspect of the invention, the measuring medium is a biological medium, in particular a seric medium.

According to another aspect of the invention, the rare-earth metal cryptate used in the method according to the invention may be covalently linked to the substituent, either directly or via a spacer arm.

When the said substituent is an oligonucleotide, direct linking may be carried out on a functional group introduced beforehand or generated on one or more atoms of a base or of a pentofuranose unit of the oligonucleotide.

In the present description, the term "functional group" denotes any function borne by the nucleotide portion or introduced onto said portion by any method known to those skilled in the art and capable of linking by covalent bonding, directly or after activation with a function present on the cryptate or on the spacer arm borne by the cryptate. Such functional groups are, in particular, $NH_2$, COOH, CHO, OH or SH functions, and also functions capable of giving covalent bonds by substitution (halides, sulfonates, epoxide) or by addition (double bonds of maleimide type). These functions are generally borne by a hydrocarbon-based chain which is itself linked to the nucleotide portion.

Methods for introducing these functional groups are described in particular in C. Kessler, Nonisotopic probing, Blotting and Sequencing, $2^{nd}$ edition, L. J. Kricka (1995), Ed. Academic press Ltd., London, p. 66–72. According to one preferred aspect of the invention, the rare-earth metal cryptate is linked to the oligonucleotide via a spacer arm. The term "spacer arm" means any means for covalently linking the oligonucleotide to the cryptate on a terminal phosphate, an atom of a purine or pyrimidine base or an atom of the sugar.

In one advantageous aspect, the said spacer arm consists of a divalent organic radical chosen from linear or branched $C_1$–$C_{20}$ alkylene groups optionally containing one or more double bonds or triple bonds and/or optionally containing one or more hetero atoms, such as oxygen, nitrogen, sulfur or phosphorus or one or more carbamoyl or carboxamido groups; $C_5$–$C_8$ cycloalkylene groups and $C_6$–$C_{14}$ arylene groups, said alkylene, cycloalkylene or arylene groups optionally being substituted with alkyl, aryl or sulfonate groups.

In particular, the spacer arm is chosen from the groups of the following formulae:

in which n=2 to 6, and —CONH—$(CH_2)_6$—, the bonding via the —CONH group taking place on the cryptate.

The rare-earth metal cryptate used in the method according to the invention consists of at least one salt of a rare-earth metal complexed with a macropolycyclic compound of formula

I in which Z is an atom with 3 or 4 valences, R is nothing or represents hydrogen, a hydroxyl group, an amino group or a hydrocarbon-based radical, the divalent radicals Ⓐ, Ⓑ and Ⓒ, are, independently of each other, hydrocarbon-based chains optionally containing one or more hetero atoms and optionally interrupted with a heteromacrocycle, at least one of the radicals Ⓐ, Ⓑ and Ⓒ also comprising at least one molecular unit or consisting essentially of a molecular unit, said molecular unit having a triplet energy greater than that of the emission level of the complexed rare-earth metal ion.

In particular, said rare-earth metal cryptate corresponds to formula (I) in which the molecular unit is chosen from phenanthroline, anthracene, benzene, naphthalene, biphenyl, terphenyl, azobenzene, azopyridine, pyridine, bipyridines, bisquinolines and the compounds having the formulae below:

—$C_2H_4$—$X_1$—$C_8H_4$—$X_2$—$C_2H_4$—
—$C_2H_4$—$X_1$—$CH_2$—$C_6H_4$—$CH_2$—$X_2$—$C_2H_4$—

$X_1$ and $X_2$, which may be identical or different, denote oxygen, nitrogen or sulfur, X being oxygen or hydrogen.

Advantageously, said rare-earth metal cryptate consists of a rare-earth metal salt complexed with one of the macrocyclic compounds below:

(22)phenanthroline; (22)phenanthroline amide; (22) anthracene; (22)anthracene amide; (22)bi-isoquinoline; (22)biphenyl-bis-pyridine; (22)bipyridine; (22) bipyridine amide; tris-bipyridine macropolycycles, tris-phenanthroline, phenanthroline-bis-bipyridine, bi-isoquinoline-bis-bipyridine, bis-bipyridine diphenylbipyridine.

Such compounds are described, for example, in patent EP 180 492.

Cryptate macropolycyclic compounds complexing rare-earth metal ions in which the molecular unit is chosen from bipyrazines, bipyrimidines and nitrogenous heterocycles comprising N-oxide groups may also be used.

Macropolycyclic compounds containing bipyrazine units are described in F. Bodar-Houillon et al., New J. Chem., 1996, 20, 1041–1045.

Macropolycyclic compounds containing bipyrimidine units are described in J. M. Lehn et al., Helv. Chim. Acta, 1992, 75, 1221.

Macropolycyclic compounds comprising nitrogenous heterocycles comprising N-oxide groups are described in J. M. Lehn et al., Helv. Chim. Acta, 1991, 74, 572.

According to another advantageous aspect, said rare-earth metal cryptate consists of at least one salt of a rare-earth metal complexed with a macropolycyclic compound corresponding to one of the formulae II and III below:

II

III in which:

the ring of formula is one of the following rings:

1)

n = 0 or 1

2)

[N$_2$O$_4$] macrocycle or ring (22)
[N$_2$O$_3$] macrocycle or ring (21)

bis-bipyridine macrocycle

Y is a group or a spacer arm which consists of a divalent organic radical, chosen from linear or branched C$_1$ to C$_{20}$ alkylene groups optionally containing one or more double bonds and/or optionally containing one or more hetero atoms such as oxygen, nitrogen, sulfur or phosphorus or one or more carbamoyl or carboxamido groups; from C$_5$ to C$_8$ cycloalkylene groups or from C$_6$ to C$_{14}$ arylene groups, said alkylene, cycloalkylene or arylene groups optionally being substituted with alkyl, aryl or sulfonate groups;

Z is a functional group capable of bonding covalently with a biological substance;

R is a methyl group or represents a group —Y—Z;

R' is hydrogen or a group —COOR" in which R" is a C$_1$ to C$_{10}$ alkyl group and preferably represents a methyl, ethyl or tert-butyl group or R' is a group —CO—NH—Y—Z.

According to one advantageous aspect, the rare-earth metal cryptate used according to the invention is a europium, terbium, samarium, dysprosium or neodymium cryptate, the europium cryptate being preferred.

In one advantageous aspect, said rare-earth metal cryptate is the europium cryptate Eu trisbipyridine or Eu[bis-diethoxybipyridine.bipyridine].

The invention is illustrated by the examples below, in which the following abbreviations will be used:

ACN: acetonitrile

BSA: bovine serum albumin

NHS/DCC: N-hydroxysuccinimide/dicyclohexylcarbodiimide

TEAB: triethylammonium bicarbonate

TEA Ac: triethylammonium acetate containing 10% acetonitrile

TFA: trifluoroacetic acid

FU: arbitrary fluorescence unit (depends on the machine used for the measurement)

EXAMPLE 1

Change in the Photophysical Properties of a Cryptate-Triphosphate Conjugate and Measurement of the Fluorescence Lifetime 1°) Preparation of a Cryptate-Triphosphate Conjugate A conjugate consisting of a [Eu3+(trisbipyridine)] unit functionalized in position 4 of a bipyridine and coupled via a spacer arm to position 5 of a 2'-deoxy-nucleoside-5'-triphosphate unit is used; this conjugate will be referred to as K-11-dUTP. The compound K-11-dUTP is prepared according to the following procedure:

In this conjugate, the number 11 indicates the total number of atoms in the spacer arm and in the functional group which links the cryptate structure to the nucleotide (in this case, the linkage takes place in position 5 of the pyrimidine).

The nucleoside-triphosphate used is 5-[N-(6-aminocaproyl)-3-aminoallyl]-2'-deoxyuridine-5'-triphosphate] (AH-dUTP) prepared by reacting N-hydroxysuccinimide trifluoroacetamidocaproate (M. S Urdea et al., Nucleic acids Res., 1988, 4937) with 5-(3-aminoallyl)-2'-deoxyuridine-5'-triphosphate prepared according to a literature process (Langer et al. Proc. Natl. Acad. Sci. USA (1981), 78, 6633–6637), followed by an ammoniacal deprotection (aqueous 3% NH$_4$OH, 45 min at 60° C.). The compound is purified on DEAE-Sepharose® (Pharmacia) in a linear gradient of triethylammonium bicarbonate (0.1 M to 0.3 M).

68 µl of a solution of AH-dUTP containing 6 µmol/ml (ie. 0.4 µmol) are diluted with 250 µl of 0.1 M pH 7.8 triethylammonium bicarbonate (TEAB) and 320 µl of an N-hydroxysuccinimide cryptate solution (4 mg/ml in acetonitrile) prepared as follows are added. The europium [(bis-bpy)(bpy-diester)] cryptate described in Example 4, section A of patent application EP 0 321 353 is hydrolyzed with NaOH and the diacid cryptate obtained is purified on an RP-18 HPLC column (gradient of acetonitrile in 1% trifluoroacetic acid in water). The europium [(bis-bpy)(bpy-diacid)] cryptate thus obtained (4 mg) is dissolved in 0.5 ml of anhydrous acetonitrile and 1 mg of N-hydroxysuccinimide is added, followed by a solution of 1.9 mg of dicyclohexylcarbodiimide dissolved in 0.5 ml of acetonitrile. After reaction for 16 h, the dicyclohexylurea precipitate is filtered off and the N-hydroxysuccinimide cryptate solution is used directly for the coupling.

After stirring for 45 min, 15 µl of 1 M pH 8.5 TEAB are added and the mixture is then injected onto a Superdex 30® HR 10/30 column (Pharmacia), eluting with 0.05M pH 7 TEAB containing 10% acetonitrile (flow rate 1 ml/min).

The compound of Rt≅16.4 min is collected and this fraction, named fraction 1, is concentrated under vacuum (speed-vac) to a volume of 350 µl and contains 8 AU$_{304}$ nm. Estimating an $\epsilon_{304}$≅35000, it is estimated that the concentration of K-dUTP is about 0.72 mM.

An aliquot (90 µl) of this fraction 1 is injected onto the same column eluted with a 25 mM pH 7 triethylammonium acetate buffer containing 5% acetonitrile. The fraction corresponding to the only peak in the chromatogram is collected (16 min<Rt<19 min) and concentrated under vacuum (speed-vac). 150 µl of a K-dUTP solution, named fraction 2, containing 1.95 AU$_{304}$ nm are obtained.

The compound is analyzed by mass spectrometry (positive mode electrospray):

(M−2H)$^+$=1431

(M−2H+CH$_3$COOH)$^+$=1491.

The UV spectrum in water shows a maximum at 241 nm characteristic of the nucleoside portion of the molecule (λmax=289 nm, $\epsilon$=7100, λmax=240 nm, $\epsilon$=10 700) and a maximum at 304 nm close to the λmax of 305 nm ($\epsilon$=30 000) characteristic of the europium cryptate. An A$_{304}$/A$_{241}$ ratio≅0.83 is observed, which is compatible with the structure proposed.

2°) Measurement of the Kinetics of Hydrolysis of a cryptate-triphosphate [trisbipyridine (Eu$^{3+}$)-11-dUTP] with Alkaline Phosphatase by Measuring the Lifetime 600 µl of a K-dUTP solution at a concentration of 1.6×10$^{-6}$ M in a 1.9 M pH 9.0 Tris buffer containing 0.1M NaCl and 15 mM MgCl$_2$ are introduced into the cuvette of an LS50 spectrofluorimeter (Perkin-Elmer).

The fluorescence intensity is measured at 620 nm, along with the fluorescence lifetime [spectrofluorimeter settings: λexcitation=305 nm, λemission=550 to 750 nm, phosphorescence mode 0.1 ms to 0.4 ms excitation slit=10 nm, emission slit=10 nm] which gives the initial value (t=0).

2 µl of a solution diluted to ¹⁄₁₀₀ of alkaline phosphatase (Boehringer) in 0.1M pH 9.0 Tris buffer, which corresponds to 2 enzymatic units, are added. After times of 15 min, 30 min, 60 min and 80 min, the fluorescence intensity at 620 nm (fluorescence spectrum) is measured, under the same conditions as above, as is the lifetime of the europium for times 30 min, 60 min and 80 min.

The values observed are given in table 1 below.

TABLE 1

| time (min) | emission at 620 nm (FU) | lifetime (ms) |
|---|---|---|
| 0 | 95 | 0.611 |
| 15 | 64 | nd |
| 30 | 47.5 | 0.568 |
| 60 | 29.8 | 0.521 |
| 80 | 24.5 | 0.51 |

Measurements of fluorescences and of lifetimes under similar conditions are carried out with a K-11-dUTP solution at a concentration of 3.7×0.10$^{-6}$ M in the above buffer, followed by addition of 1 µl of alkaline phosphatase diluted to ¹⁄₁₀ in 0.1 M pH 9.0 Tris buffer, which corresponds to 10 enzymatic units.

Before adding the enzyme, a lifetime of 0.61 ms is observed; after adding the enzyme, it is observed that the lifetime decreases very rapidly and stabilizes to give a final value of 0.41 ms.

By way of reference, the spectrum and lifetime of an [Eu3+(tris-bipyridine)] cryptate functionalized simply with a spacer arm, referred to hereinbelow as KNH$_2$, are measured. It is observed that the lifetime of the KNH$_2$ in the 0.1M pH 9.0 Tris buffer is 0.39 ms.

Figure 1:
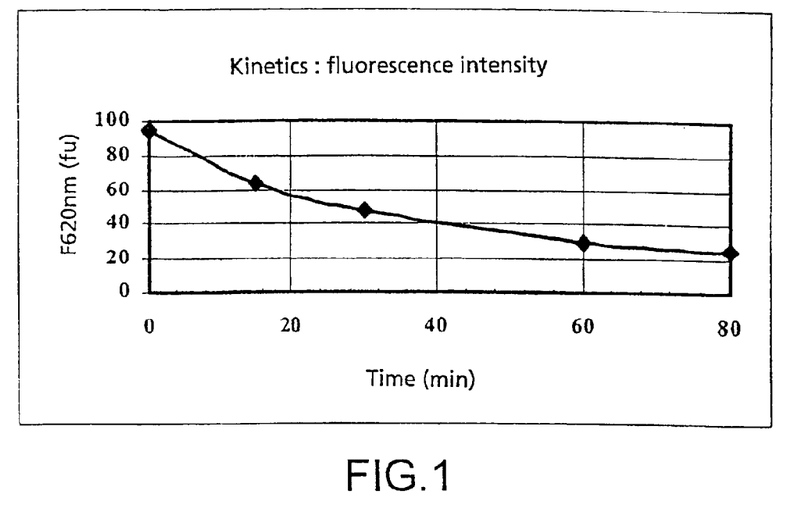
Figure 2:
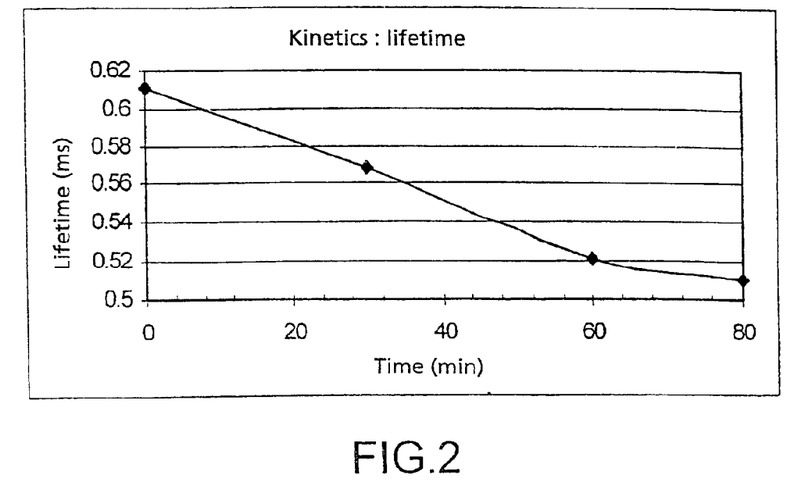

Graphs of the kinetics of the fluorescence intensity and of the lifetime are represented, respectively, in FIGS. 1 and 2.

It is thus observed that the enzymatic hydrolysis of the triphosphate chain to give inorganic phosphorus is accompanied by a decrease in the fluorescence intensity and a decrease in the lifetime. The kinetics of decrease of the lifetime (which is independent of the concentration of florescent compound) are a function of the enzymatic activity; they are faster if the number of enzymatic units introduced is increased.

The final value of the lifetime t=0.41 ms after hydrolysis of the K-dUTP tends towards the value of 0.39 ms observed for the unconjugated cryptate.

Hydrolysis of the phosphate groups thus changes the environment of the europium cryptate and modifies its photophysical properties.

EXAMPLE 2

Change in the Photophysical Properties of a Cryptate-Triphosphate Conjugate and Time-Resolved Measurement of the Fluorescence Intensity A solution of K-11-dUTP prepared as indicated in Example 1 at a concentration of $3 \times 10^{-6}$ M in a 0.1 M pH 9.0 Tris buffer containing 0.1 M NaCl and 15 mM $MgCl_2$ is prepared. In parallel, a solution of $KNH_2$ at a concentration of $3 \times 10^{-6}$ M in the same buffer is prepared.

Each solution is diluted to 1/500 M in the same buffer and 200 µl of the dilute K-11-dUTP solution are placed in 2 rows of 10 wells of a black-bottomed microplate. In the same way, 200 µl of the dilute $KNH_2$ solution are placed in 2 other rows of 10 wells of the microplate.

The fluorescence is read at 620 nm (using a window from 50 to 400 µs) for the various wells by means of a time-resolved fluorimeter (Discovery) to find the fluorescence values at $t_0=0$.

2 µl of buffer are added to each of the wells of a row containing the K-11-dUTP (referred to as KTP-T) and of a row containing the $KNH_2$ (referred to as K-T), 2 µl of an alkaline phosphatase solution diluted to 1/100 (see Example 1) are added to each of the wells of the other row containing the K-dUTP (referred to as KTP-E) and of the other row containing the $KNH_2$ (referred to as K-E). The averages of the fluorescence values of each row are taken.

The measurements are carded out at 620 nm at the end of 10 min, 35 min and 70 min. The ratio $(F_t/F_0)$ of the fluorescence (Ft) at time t to the fluorescence ($F_0$) at $t_0$ is measured.

The results are given in Table 2 below.

TABLE 2

| time (min) | KTP-T | T $(F_t/F_0)$ | KTP-E | R $(F_t/F_0)$ |
|---|---|---|---|---|
| 0 | 174970 | 1 | 190100 | 1 |
| 10 | 193500 | 1.11 | 141900 | 0.75 |
| 35 | 198000 | 1.13 | 68000 | 0.36 |
| 70 | 195000 | 1.11 | 41500 | 0.22 |

The results show that in the presence of the enzyme, the fluorescence intensity at 620 nm decreases over time. This change takes place at a speed comparable to that which might be expected for the enzymatic hydrolysis of the phosphate groups of a nucleoside triphosphate under the chosen experimental conditions.

Moreover, it is observed that the fluorescence in the $KNH_2$ wells with enzyme (K-E) is at the same intensity as in the control $KNH_2$ wells (K-T) without enzyme and that, in both cases, the fluorescence varies very little over time, which shows that the cryptate by itself is not modified by the presence of the enzyme.

These results confirm that the hydrolysis of the phosphate chain of K-11-dUTP causes a change in the photophysical properties of the rare-earth metal cryptate.

EXAMPLE 3

Preparation of the [trisbipyridine(Eu3+)-aminohexyl phosphate cryptate

1°) Preparation of a [trisbipyridine(Eu3+)-aminohexyl phosphate (KAH-PO4) cryptate conjugate:

2 mg (10 µmol) of aminohexyl phosphate (Sigma) are dissolved in 100 µl of 0.1 M pH 7.8 triethylammonium bicarbonate (TEAB) and 100 µl of a solution of activated [TBP-(Eu3+)] cryptate (4 mg/ml in acetonitrile), ie. 0.26 µmol, are added. The activated [TBP-(Eu3+)] cryptate (NHS/DCC) in acetonitrile as described in Example 1, 1) above is prepared at the time of use from the europium [(bis-bipy)-(bipy-diacid)] cryptate which is itself obtained from the europium [(bis-bipy)-(bipy-dimethyl ester)] cryptate described in Example 4, section A, of patent application EP 0 321 353.

After stirring for 15 min, the mixture is concentrated to half its volume and then injected onto a Superdex peptide HR 10/30 column (Pharmacia), eluting with 25 mM pH 9 TEA Ac containing 10% acetonitrile (flow space rate 1 ml/min).

The compound of Rt≅19 min is collected; this fraction is concentrated under vacuum (speed-vac) to a volume of about 300 µl. This solution of purified KAH-PO4 contains 0.2 µmol of cryptate and will be used for the photophysical measurements. This fraction is analyzed on the same Superdex peptide column eluted with a 25 mM pH 7 triethylammonium acetate buffer containing 10% acetontrile. A single peak of Rt≅20 min is observed. Co-injection with the europium [(bis-bipy) (bipy-diacid)] cryptate shows that this cryptate migrates with an Rt≅23.7 min. Similarly, the KAH-PO4 is analyzed by RP18-HPLC (Merck) in a gradient of acetonitrile in an aqueous solution containing 1% TFA (15% ACN isocratic for 5 min and then linear gradient from 15 to 100% ACN over 30 min). A peak at Rt≅16.6 min is observed, which is different than the europium [(bis-bipy) (bipy-diacid)] cryptate, which migrates with an Rt≅15.9 min.

2°) Photophysical Properties of the KAH-PO4 Conjugate:

Starting with the aqueous KAH-PO4 solution prepared as above, a solution diluted to $1.5 \times 10^{-5}$ M of KAH-PO4 in a 0.1 M pH 9.0 Tris buffer containing 0.1 M NaCl and 15 mM $MgCl_2$ is prepared.

The fluorescence intensity at 620 nm and the fluorescence lifetime are measured [spectrofluorimeter settings: λexcitation=305 nm, λemission=550 to 750 nm, phosphorescence mode 0.1 ms to 0.4 ms, excitation slit=10 nm, emission slit=10 nm], which gives the initial value (t=0).

A lifetime t=0.637 ms is observed.

It is noted that, under the same conditions, the europium [(bis-bipy)-(bipy-diacid)] cryptate has a lifetime t=0.21 ms.

3°) Kinetics of Phosphate Cleavage:

The solution of KAH-PO4 in Tris buffer described above is used and 2 µl of a solution diluted to 1/100 of alkaline phosphatase (Boehringer) in 0.1M pH 9.0 Tris buffer, which corresponds to 2 enzymatic units, are then added.

The fluorescence intensity and lifetime measurements are then carried out at the times indicated in Table 3 below:

TABLE 3

| Time (min) | Intensity 620 nm | Lifetime (ms) |
|---|---|---|
| 0 | 130 | 0.633 |
| 5 | 86 | 0.597 |
| 10 | 74 | 0.578 |
| 15 | 64 | 0.566 |
| 20 | 55 | 0.555 |
| 30 | 48 | 0.529 |
| 46 | 41 | 0.514 |
| 60 | 37 | 0.504 |
| 75 | 34 | 0.495 |
| 75 | 34 | 0.495 |

The reaction mixture is then left for 16 h at 20° C. in order for the enzymatic reaction to be complete. A lifetime t=0.45 ms is then observed.

A change in the photophysical properties is observed in the course of the hydrolysis of the phosphate functions. During the reaction, the lifetime tends towards the value of the lifetime (t=0.39 ms) observed for $KNH_2$ in the same medium.

EXAMPLE 4

Hydrolysis of a [trisbipyridine(Eu3+)]-oligonucléotide Cryptate Conjugate with phosphatase/phosphodiesterase 1°) Labeling of an Oligodeoxynucleotide with a Cryptate:

An oligodeoxynucleotide (ODN) of $^{5'}d(T_{10}G_4C^{AH}G)_3{'}$ modified close to its 3' end with an aminohexyl (AH) arm is synthesized on a solid support by the "phosphite-phosphoramidite" method using a DNA synthesizer (Applied Biosystems type 392) according to the manufacturer's protocol. A modified nucleotide is introduced by coupling on a CPG support grafted with deoxyguanosine (Perkin Elmer/Applied Biosystems), with an N,N-diisopropyl-βcyanoethyl phosphoramidite derivative obtained from 5'-O-(4,4'-dimethoxytrityl)-N-4-(6-trifluoracetamidohexyl)-2'-deoxycytidine prepared by trifluoroacetylation of 5'-O-(4,4'-dimethoxytrityl)-N-4-(6-aminohexyl)-2'-deoxycytidine [ROGET et al. Nucleic Acids Res., 17, 7643–7650, (1989)]. The synthesis of the above sequence is then continued. At the end of the synthesis on a DNA synthesizer in "trityl-on" mode, the oligonucleotide is treated with concentrated aqueous ammonia (16 h at 55° C.) and purified by HPLC on a LiChrospher® RP-18E 250-10 (10 µm) column (Merck, Germany) with a gradient of acetonitrile in 50 mM triethylammonium acetate (buffer A: 5% acetonitrile, buffer B: 50% acetonitrile; flow rate 5 ml/min, gradient from 10% B to 60% B over 20 min, isocratic 60% B for 5 min and then gradient from 60% B to 100% B over 5 min) (Oligonucleotide synthesis: A practical approach. Ed M. J. Gait. IRL Press, Oxford). The fractions corresponding to a major peak (retention time greater than 20 min) are evaporated. After evaporation and coevaporation with water, the partially deprotected oligonucleotide thus obtained is detritylated with 80% acetic acid (ambient temperature, 30 min), after evaporation and coevaporation, the fully deprotected oligonucleotide is taken up in 50 µl of 100 mM pH ~8 triethylammonium bicarbonate (TEAB) and precipitated with 1.5 ml of n-butanol. After centrifugation, the supernatant is removed and the precipitate dried under vacuum is taken up in 200 µl of water. This stock solution (oligonucleotide referred to as AH-ODN1) is used for the cryptate labeling.

2°) Coupling of a [TBP-(Eu3+)] cryptate Molecule with an oligodeoxynucleotide Functionalized with an aminohexyl Arm (AH-ODN1):

An aliquot portion of the stock solution of the oligonucleotide obtained above is diluted with 150 µl of aqueous 0.1 M pH 7.8 triethylammonium bicarbonate (TEAB) solution and 60 µl of an activated [TBP-(Eu3+)] cryptate solution (4 mg/ml), ie. 171 nmol (about 4 equivalents), are added. The activated [TBP-(Eu3+)] cryptate (NHS/DCC) is prepared at the time of use from europium [(bis-bipy)-(bipy-diacid)] cryptate which is itself obtained from the europium [(bis-bipy)-(bipy-dimethyl ester)] cryptate described in Example 4, section A, of patent application EP 0 321 353.

After stirring for 30 min, 15 µl of 1 M pH 8.5 TEAB are added and the mixture is then evaporated under vacuum (speed-vac) to a volume of 200 µl, deposited on an NAP10 column (Pharmacia) equilibrated in 25 mM pH 7 TEA Ac buffer containing 10% acetonitrile, and eluted with the same buffer according to the manufacturer's protocol, the fraction excluded is collected in a volume of 1 ml and this fraction is concentrated (speed-vac) to a volume of 200 µl.

3°) Purification of the Conjugate Formed from a [TBP-(Eu3+)]cryptate and from an oligodeoxynucleotide Functionalized with an aminohexyl Arm (KH-ODN1 Conjugate):

The KH-ODN1 conjugate is analyzed by FPLC on a mono-Q column (Pharmacia) using the following conditions (buffer A: 20 mM pH 5 sodium acetate containing 10% acetonitrile. Buffer B: 20 mM pH 5 sodium acetate 1 M lithium chloride containing 10% acetonitrile. Gradient: 0 to 2 min isocratic 20% B, 2 min to 30 min gradient from 20% B to 60% B, flow rate 1 ml/min).

All of the excluded fraction obtained from the NAP10 column (200 µl) is then injected onto the mono-Q column, the fraction corresponding to the K-ODN1 conjugate is collected, concentrated to 300 µl and desalified on an NAP10 column equilibrated in 25 mM pH 7 TEAAc buffer containing 10% acetonitrile. The column is eluted with the same buffer according to the manufacturers protocol and the excluded fraction is collected in a volume of 1 ml. This fraction corresponding to pure KH-ODN1 conjugate is characterized by an ultraviolet spectrum having a maximum at 260 nm (ODN component) and a shoulder at about 305 nm (cryptate component). A nucleotide labeled with cryptate on the aminohexyl arm attached in position 4 of the cytosine close to the 3' end [sequence $^{5'}$-d$(T_{10}G_4C^{KAH}G)_3{'}$ referred to as K-ODN1] is thus obtained.

4°) A Stock Solution of the K-ODN1 Conjugate is Used, and this Stock Solution is Diluted in PBS Buffer Containing 0.1% BSA.

100 µl of the dilute solution are placed in the wells of a microtitration plate. 100 µl of buffer are placed in the first two wells and 100 µl of a dilute uric acid solution prepared such that the final concentration of uric acid increases by a factor of 2 from one well to the next, according to Table 4 below, are placed in the following wells.

The fluorescent intensity is measured at 620 nm on a Discovery machine, and the results are given in Table 4 below. The percentage of extinction (quenching) relative to the control containing no uric acid is calculated via the following relationship:

$$100-100[E_{620} \text{ (uric acid}/E_{620} \text{ (standard 0)}]$$

TABLE 4

| [uric acid] final (mg/l) | E620 (fu) | Extinction (%) |
|---|---|---|
| 0 | 134464 | 0 |
| 1.25 | 128729 | 4.3 |
| 2.5 | 132572 | 1.4 |
| 5 | 120999 | 10 |
| 10 | 116689 | 13.22 |
| 20 | 111623 | 17.0 |
| 40 | 105703 | 21.4 |
| 80 | 104481 | 22.3 |

The same series of measurements is carried out after increasing incubation times (indicated in hours) and the extinction (%) is measured in the same way as a function of the uric acid concentration.

The results are collated in Table 5 below.

TABLE 5

| | Extinction (%) | | | |
|---|---|---|---|---|
| [uric acid] final (mg/l) | t = 0 | t = 3.5 h | t = 5.5 h | t = 16 h |
| 0 | 0 | 0 | 0 | 0 |
| 1.5 | 14 | 13 | 15 | 18 |
| 3.1 | 15 | 17 | 22 | 45 |
| 6.2 | 18 | 19 | 24 | 54 |
| 12.5 | 16 | 26 | 32 | 63 |
| 25 | 25 | 24 | 33 | 72 |
| 50 | 20 | 25 | 34 | 75 |
| 100 | 23 | 34 | 42 | 77 |

The results show that for a given concentration of uric acid (50 mg/l) which causes a low extinction of the fluorescence of the cryptate when it is coupled to the oligonucleotide (about 20%), an increase in the extinction up to about 75% is observed over time, at a time corresponding to a complete digestion of the oligonucleotide.

The digestion of the oligonucleotide to give nucleosides is thus accompanied by a variation in the photophysical properties of the cryptate and an increase in its quenching sensitivity.

These results show the possibility of monitoring the progress of a reaction by means of the change in the photophysical properties (such as the extinction) of a fluorescent label in the presence of an extinction agent introduced into the reaction medium.

EXAMPLE 5

Changes in the Photophysical Properties of a [trisbipyridine(Eu3+)]-oligonucleotide cryptate Conjugate in the Course of a Hybridization 1°) Labeling of an ODN AH-kras12M1 with cryptate An oligonucleotide of sequence 5'-d($^{AH}$C ACG CCA CTA GCT CC)$_3$' modified at its 5' end with an aminohexyl (AH) arm synthesized on a solid support is used.

Following the labeling protocol of Example 4, an oligonucleotide labeled with cryptate on the aminohexyl arm attached in position 4 of the cytosine derivative located at the 5' end [sequence $^5$'d(C$^{KAH}$ ACG CCA CTA GCT CC)$_{3'}$ referred to as K-ODN2] is obtained in this case.

2°) The oligonucleotide ODN3 of Sequence $^5$'d (GGAGCTAGTGGCGT)$_{3'}$, which is Complementary to the K-ODN2 Sequence Described Above, is Synthesized.

3°) Comparison of the Lifetime of an Oligonucleotide Cryptate Conjugate in a Single-Stranded Form and in a Double-Stranded Form:

A solution containing equivalent amounts of the oligonucleotide K-ODN2 and its complementary sequence are placed under denaturing conditions (95° C., 5 min) in a 0.1 M NaCl phosphate buffer, and hybridization is then promoted by incubating for 20 min at 30° C.

The fluorescence lifetime of the cryptate is measured in the case of the single-stranded K-ODN2 oligonucleotide and also in the case of the K-ODN2 oligonucleotide hybridized with its complementary sequence. The measurements are carried out in pH 7 phosphate buffer containing 0.1 M NaCl, at 20° C. on an LS50 machine (Perkin Elmer).

On the LS50 machine, the decrease of a fluorescence signal (time-resolved measurement) makes it possible from the measurements to calculate the lifetime from the linear relationship linking the logarithm of the intensities and the time. The linearity of this relationship is estimated by calculating the correlation coefficient (least squares method) using the software provided with the machine.

A correlation coefficient of greater than 0.999 reflects a monoexponential decrease and the presence of a population of molecules that are homogeneous as regards their lifetime, whereas a smaller coefficient generally denotes the coexistence of two different species in the medium.

The following result is observed:

| | t (ms) | Correlation coefficient |
|---|---|---|
| K-ODN2 | 1.282 | 0.9995 |
| K-ODN2 + ODN3 | 0.565 | 0.9992 |

After 15 min at 60° C., i.e. above the Tm (characteristic melting point of a nucleic acid=temperature at which half of the molecules are in the form paired with their complementary sequence), the following results are observed:

|  | t (ms) | Correlation coefficient |
| --- | --- | --- |
| K-ODN2 | 1.043 | 0.9980 |
| K-ODN2 + ODN3 | 0.790 | 0.9956 |

The Tm value for the hybridization of K-ODN$_2$ with its complementary sequence under the conditions used herein, as estimated by an empirical formula which takes into account the length of the oligonucleotide, the NaCl concentration and the proportion of guanine and cytosine (J. Sambrook et al., Molecular Cloning, $2^{nd}$ edition 1989, Cold Spring Harbor Laboratory Press, § 11.46) is about 30° C.

After returning to the initial conditions (favorable to hybridization) the following results are observed:

|  | t (ms) | Correlation coefficient |
| --- | --- | --- |
| K-ODN2 | 1.205 | 0.9991 |
| K-ODN2 + ODN3 | 0.533 | 0.9991 |

It is observed that, in the case of the single-stranded K-ODN2 oligonucleotide, the lifetime is still longer than in the case of K-ODN2 in double-stranded form.

In the case of K-ODN2 in double-stranded form, the lifetime increases as the temperature increases, the lifetime observed being the result of the value close to 1.20 ms observed for the single-stranded form and the value close to 0.5 ms observed for the double-stranded form (the value of the correlation coefficient indicates the presence of two species).

After a denaturing cycle, returning to the conditions favorable to hybridization makes it possible to observe a decrease in the lifetime of the double-stranded form.

EXAMPLE 6

Changes in the Extinction Sensitivity of a [tris-bipyridine(Eu3+)]-oligonucleotide cryptate Conjugate in the Course of a Hybridization The oligonucleotides K-ODN2 and ODN3, the structures and syntheses of which are described in example 5, are used.

A stock solution of the conjugate K-ODN2 is prepared. This stock solution is diluted in PBS buffer containing 0.1% BSA so as to obtain a solution containing about $1.5 \times 10^{-8}$ M of cryptate. In parallel, a stock solution of the K-ODN2 conjugate hybridized with its complementary sequence (ODN3) is prepared. This stock solution is diluted in PBS buffer containing 0.1% BSA so as to obtain a solution also containing about $1.5 \times 10^{-8}$ M of cryptate.

100 µl of the dilute solution are placed in the wells of a microtitration plate, 100 µl of buffer are added to the first two wells and 100 µl of a dilution of uric acid in PBS buffer, prepared such that the final uric acid concentration increases by a factor of 2 from one well to the next according to table 6 below, are placed in the following wells.

The fluorescence intensity is measured at 620 nm for the various wells at ambient temperature (20° C.) on a Discovery machine (time-resolved measurement with a window from 50 to 400 µs). The results are given in table 6 below, and the extinction relative to the control containing no uric acid is calculated.

TABLE 6

Extinction with uric acid at 20° C.

| [uric acid] | Single-stranded K-ODN | | Double-stranded K-ODN | |
| --- | --- | --- | --- | --- |
| final (mg/l) | E620 (fu) | Extinction (%) | E620 (fu) | Extinction (%) |
| 0 | 134464 | 0 | 170792 | 0 |
| 1.25 | 128729 | 4.3 | 150359 | 12 |
| 2.5 | 132572 | 1.4 | 122602 | 28.2 |
| 5 | 120999 | 10 | 103991 | 39 |
| 10 | 116689 | 13.22 | 72621 | 57.5 |
| 20 | 111623 | 17 | 57258 | 66.5 |
| 40 | 105703 | 21.4 | 41272 | 75.8 |
| 80 | 104481 | 22.3 | 34824 | 79.6 |

The plate is then incubated for 15 min at 60° C. and the fluorescent entities are immediately measured at 620 nm for the various wells at a temperature of 60° C. on a Discovery machine (time-resolved measurement with a window from 50 to 400 µs). The results are given in table 7 below, and the extinction relative to the control containing no uric acid is calculated.

TABLE 7

Extinction of uric acid at 60° C.

| [uric acid] | Single-stranded K-ODN | | Double-stranded K-ODN | |
| --- | --- | --- | --- | --- |
| final (mg/l) | E620 (fu) | Extinction (%) | E620 (fu) | Extinction (%) |
| 0 | 65373 | 0 | 71357 | 0 |
| 1.25 | 61383 | 6.1 | 67168 | 5.9 |
| 2.5 | 61048 | 6.6 | 59702 | 16.3 |
| 5 | 57930 | 11.4 | 57534 | 19.4 |
| 10 | 53767 | 17.8 | 57561 | 19.3 |
| 20 | 48357 | 26.0 | 54074 | 24.2 |
| 40 | 46817 | 28.4 | 52864 | 25.9 |
| 80 | 47879 | 26.8 | 50103 | 29.8 |

These results confirm that the sensitivity of the cryptate with respect to the extinction phenomenon is different for a cryptate-oligonucleotide conjugate when it is in double-stranded and single-stranded form. Uric acid is an extinction agent which is specific for the double-stranded form.

The hybridization phenomenon may thus be monitored by measuring the time-resolved fluorescence in the presence of a compound allowing a selective extinction of the hybridized species.

EXAMPLE 7

Change in the Photophysical Properties During the Hydrolysis of Ester Functions

1°) Preparation of the N-hydroxysuccinimide Ester

An N-hydroxysuccinimide ester is used, which has the advantage of being hydrolyzed spontaneously in water at a pH of 7, at a rate which is slow enough to facilitate the fluorescence measurements and to allow kinetic monitoring of the photophysical properties in a simple manner.

A [tris-bipyridine($Eu^{3+}$)]-bis-aminoethylcarboxamide cryptate derivative (product referred to as KNH2 in example 1), obtained by aminolysis in the presence of ethylenediamine of the europium [(bis-bipy)-(bipy-diethyl ester)] cryptate described in example 4, section A, of patent application EP 0 321 353 (Mathis G. and Lehn J. M.), is used.

This cryptate is reacted with an excess of DSS (bis(N-hydroxysuccinimide ester of suberic acid, Sigma).

The KNH2 derivative characterized on HPLC by an Rt of 12.3 min is converted into NHS ester [K-di(NHS-suberate)] showing an Rt of 17.2 min [HPLC analytical conditions, Lichrospher (Merck) RP-18 (5µ) 1254 column, elution with 1 ml/min solvent A: 1% TFA in $H_2O$; solvent B: pure acetonitrile. Gradient from 15% B to 32% B over 30 min].

The cryptate thus obtained bearing two ester functions [K-di(NHS-suberate)] is purified by preparative HPLC on a Lichrospher (Merck) RP-18 (10µ) 250-10 column, elution at 5 ml/mn [solvent A: 1% TFA in $H_2O$; solvent B: pure acetonitrile. Gradient from 15% B to 32% B over 30 min]. The fraction containing the pure ester is evaporated under vacuum and then dried, and an HPLC analysis (analytical conditions above) shows a retention time of 17.2 min.

In a similar manner, the NHS ester [K-mono-NHS-suberate)] is prepared, starting with a [trisbipyridine($Eu^{3+}$)] mono-aminoethylcarboxamide cryptate derivative obtained by aminolysis in the presence of ethylenediamine of the europium [(bis-bipy)-(bipy-monoethyl ester)] cryptate, which is itself prepared by partial saponification (aqueous NaOH and then RP-HPLC purification) of the europium [(bis-bipy)-(bipy-diethyl ester)] cryptate described in example 4, section A of patent application EP 0 321 353.

This ester is purified by preparative RP-HPLC (above conditions), and the fraction containing the pure monoester (Rt=15.6 min) is rapidly evaporated under vacuum. This monoester will be used to study the change in the fluorescence properties in the course of the hydrolysis.

By HPLC analysis in the above gradient, it is observed that, in aqueous solution or in solution buffered to pH 7, the diester is converted into monoacid derivative of Rt=16.0 min and then into diacid derivative of Rt=14.8 min. In water, a greater than 50% hydrolysis is observed in 3 h.

By HPLC analysis in the above gradient, it is observed that, in aqueous solution or in solution buffered to pH 7, the monoester of Rt=15.6 is converted into its acid derivative of Rt=14.2 min. In water, a greater than 50% hydrolysis is observed in 3 h.

2°) Change in the Fluorescence Spectra During the Hydrolysis of an N-hydroxysuccinimide ester of [tris-bipyridine($Eu^{3+}$)] cryptate The fluorescence emission spectra and the fluorescence lifetime of K-NHS-suberate cryptate are recorded in aqueous solution, by carrying out a measurement just after the dilution and then after 20 h. Under the same conditions, the spectra of a KNH2 solution used as reference (solution of equivalent concentration) is recorded. It is confirmed that the fluorescence intensity emitted at 620 nm of this reference does not vary by more than 2% over 20 h and that the lifetime is not modified (variation<0.3%). The results are given in table 7 below:

TABLE 7

| time (h) | E 620 (fu) | Variation E 620 (%) | Total fluorescence (area) | Variation in total fluorescence (%) | Lifetime (µs) | Correlation coefficient |
|---|---|---|---|---|---|---|
| 0 | 81.8 | — | 1475 | — | 376 | 0.9999 |
| 20 | 96.0 | +17.6 | 2198 | +49% | 458 | 0.9999 |

It is observed that, during the hydrolysis of the ester function, the photophysical properties such as the emission intensity or the fluorescence lifetime are modified.

What is claimed is:

1. A homogeneous method for detecting and/or determining by fluorescence a chemical or physicochemical interaction in a measuring medium, in which a rare-earth metal cryptate comprising a substituent is used, characterized in that the variation of at least one fluorescence characteristic of the rare-earth metal cryptate, induced by the change in the physicochemical properties of the substituent resulting from said interaction, is measured.

2. The method as claimed in claim 1, characterized in that said change has an influence on the salvation sphere of the rare-earth metal ion.

3. The method as claimed in claim 1, characterized in that the fluorescence characteristic is chosen from the emission lifetime, the fluorescence intensity, the distribution of the lines in the fluorescence spectrum and the polarization.

4. The method as claimed in claim 1, characterized in that the variation is an increase or a decrease in the emission lifetime or the fluorescence intensity.

5. The method as claimed in claim 4, characterized in that the variation is due to an agent which induces a fluorescence enhancement or extinction.

6. The method as claimed in claim 1, characterized in that said substituent is negatively charged or acquires a negative charge in the course of a physicochemical process.

7. The method as claimed in claim 1, characterized in that said substituent in a phosphate, phosphonate or carboxylate group or a derivative thereof, or a chemical or biological molecule comprising this group.

8. The method as claimed in claim 7, characterized in that said molecule is a nucleic acid, an oligonucleotide or an oligonucleotide consisting of or comprising nucleotide analogs; a nucleotide or a nucleoside and analogs thereof.

9. The method as claimed in claim 1, characterized in that said interaction results from an enzymatic reaction.

10. The method as claimed in claim 1, characterized in that said interaction consists of a hybridization or denaturing reaction of nucleic acids, of oligonucleotides or of oligonucleotides consisting of or comprising nucleotide analogs or of a reaction between said nucleic acids or oligonucleotides with proteins having an affinity for them.

11. The method as claimed in claim 1, characterized in that the rare-earth metal cryptate is linked covalently to the substituent, either directly or via a spacer arm.

12. The method as claimed in claim 1, characterized in that said rare-earth metal cryptate consists of at least one salt of a rare-earth metal complexed with a macropolycyclic compound of formula

In which Z is an atom with 3 or 4 valences, R is nothing or represents hydrogen, a hydroxyl group, an amino group or a hydrocarbon-based radical, the divalent radicals Ⓐ, Ⓑ and Ⓒ are, independently of each other, hydrocarbon-based chains optionally containing one or more hetero atoms and optionally interrupted with a heteromacrocycle, at least one of the radicals Ⓐ, Ⓑ and Ⓒ, also comprising at least one molecular unit or consisting essentially of a molecular unit, said molecular unit having a triplet energy greater than that of the emission level of the complexed rare-earth metal ion.

13. The method as claimed in claim 12, characterized in that the rare-earth metal cryptate consists of a salt of a rare-earth metal complexed with one of the macrocyclic or macropolycyclic compounds below:

(22)phenanthroline; (22)phenanthroline amide; (22)anthracene; (22)anthracene amide; (22)bi-isoquinoline; (22)biphenyl-bis-pyridine, (22)bipyridine; (22)bipyridine amide; tris-bipyridine macropolycycles, tris-phenanthroline, phenanthroline-bis-bipyridine, bi-isoquinoline-bis-bipyridine, bis-bipyridine diphenylbipyridine; a macropolycyclic compound comprising a molecular unit chosen from bipyrazines, bipyrmidines and nitrogenous heterocycles comprising N-oxide groups.

14. The method as claimed in claim 1, characterized in that the rare-earth metal cryptate consists of at least one salt of a rare-earth metal complexed with a macropolycyclic compound corresponding to one of the formulae II and III below:

in which:

the ring of formula is one of the following rings:

1)

n = 0 or 1

[N₂O₄] macrocycle or ring (22)
[N₂O₃] macrocycle or ring (21)

2)

bis-bipyridine macrocycle

Y is a group or a spacer arm which consists of a divalent organic radical, chosen from linear or branched $C_1$ to $C_{20}$ alkylene groups optionally containing one or more double bonds and/or optionally containing one or more hetero atoms such as oxygen, nitrogen, sulfur or phosphorus or one or more carbamoyl or carboxamido groups; from $C_5$ to $C_8$ cycloalkylene groups or from $C_6$ to $C_{14}$ arylene groups, said alkylene,k cyclcoalkylene or arylene groups optionally being substituted with alkyl, aryl or sulfonate groups;

Z is a functional group capable of bonding covalently with a biological substance;

R is a methyl goup or represents a group —Y—Z;

R' is hydrogen or a group —COOR" in which R" is a $C_1$ to $C_{10}$ alkyl group and preferably represents a methyl, ethyl or tert-butyl group or R' is a group —CO—NH—Y—Z.

15. The method as claimed in claim 1, characterized in that the rare-earth metal cryptate is a europium, terbium, samarium, dysprosium or neodymium cryptate.

16. The method as claimed in claim 15, characterized in that the rare-earth metal cryptate is the europium cryptate Eu tris-bipyridine or Eu[bis-diethoxybipyridine.bipyridine].

* * * * *

UNITED STATES PATENT AND TRADEMARK OFFICE
CERTIFICATE OF CORRECTION

PATENT NO. : 6,878,552 B1
DATED : April 12, 2005
INVENTOR(S) : Gerard Mathis et al.

It is certified that error appears in the above-identified patent and that said Letters Patent is hereby corrected as shown below:

Column 18,
Line 26, reads "salvation" should read -- solvation --
Line 44, reads "in" should read -- is --

Column 19,
Line 9, reads "In" should read -- in --
Line 25, reads "pyridine," should read -- pyridine; --
Line 30, reads "bipyrmidines" should read -- bipyrimidines --

Column 20,
Line 49, reads "alkylene,k cyclcoalkylene" should read -- alkylene, cycloalkylene --

Signed and Sealed this

Ninth Day of August, 2005

JON W. DUDAS
*Director of the United States Patent and Trademark Office*